United States Patent [19]

Lee et al.

[11] 4,454,288

[45] Jun. 12, 1984

[54] SURFACE TREATMENT OF INORGANIC FILLERS

[75] Inventors: Kenneth M. Lee, Bay City; Katherine L. Ulman, Sanford, both of Mich.

[73] Assignee: Dow Corning Corporation, Midland, Mich.

[21] Appl. No.: 446,297

[22] Filed: Dec. 2, 1982

[51] Int. Cl.$^3$ .............................................. C08L 83/00
[52] U.S. Cl. .................................... 524/588; 524/493; 524/860; 524/866; 427/387; 428/447
[58] Field of Search .............. 524/493, 588, 860, 866; 427/387; 428/447

[56] References Cited

U.S. PATENT DOCUMENTS

| | | | |
|---|---|---|---|
| 2,706,724 | 4/1955 | Bass | 260/46.5 |
| 2,909,549 | 10/1959 | Bailey | 260/448.8 |
| 2,927,909 | 3/1960 | Lyons et al. | 260/42 |
| 2,954,357 | 9/1960 | Fekete | 260/29.1 |
| 3,024,126 | 3/1962 | Brown | 106/308 |
| 3,305,524 | 2/1967 | Brown, Jr. et al. | 524/588 |
| 3,341,489 | 9/1967 | Simpson | 524/588 |
| 3,876,605 | 4/1975 | Itoh et al. | 524/588 |
| 3,979,546 | 9/1976 | Lewis | 428/394 |
| 4,228,054 | 10/1980 | Ona et al. | 260/29.2 M |
| 4,344,800 | 8/1982 | Lutz | 106/309 |

FOREIGN PATENT DOCUMENTS 1364248 10/1974 United Kingdom .

*Primary Examiner*—Melvyn I. Marquis
*Attorney, Agent, or Firm*—Richard E. Rackoczy

[57] ABSTRACT

This invention relates to a method of surface treating particulate inorganic fillers with a surface-treating agent which is an equilibrated reaction mixture consisting essentially of $R_2SiO_{2/2}$ units, $RSiO_{3/2}$ units and $CH_3O_{1/2}$ radicals wherein the mixture contains A moles of $R_2SiO_{2/2}$ units per mole of $RSiO_{3/2}$ units and B moles of $CH_3O_{1/2}$ radicals, A having an average value of from 0.5 to 10 and B having an average value of from 3 to 6, the value of B being related to A such that when $A=0.5$, $B=6$ and when $A=10$, $B=3$, and R being a hydrocarbon radical of from 1 to 10 inclusive carbon atoms or a haloalkyl radical of from 1 to 10 inclusive carbon atoms. Reinforcing silica fillers, surface-treated with such equilibrated reaction mixtures can be compounded with polydiorganosiloxanes curable to elastomers and cured to obtain silicone elastomers possessing high optical clarity and physical properties which make the cured elastomer uniquely suitable for use as prosthetic devices for use on or within the body.

27 Claims, No Drawings

SURFACE TREATMENT OF INORGANIC FILLERS

This invention relates to a method of surface treating particulate inorganic fillers with an equilibrated reaction mixture composed of a particular ratio of siloxane units bearing methoxy radicals, to the surface-treated fillers themselves and to polysiloxane compositions and cured silicone elastomer articles of manufacture containing such fillers.

BACKGROUND OF THE INVENTION

Various types of organosilanes and polyorganosiloxanes such as hydroxyl-endblocked polydimethylsiloxanes have been employed to surface treat the surfaces of particulate inorganic fillers, particularly reinforcing silica fillers, to render the surfaces of the fillers hydrophobic. As a result the handling properties of the uncured elastomer (filler-gum) composition are improved and the tendency for the composition to crepe harden is reduced. The physical properties such as tensile strength of the cured elastomers may also be improved.

For example, U.S. Pat. No. 2,954,357 (Fekete, issued Sept. 27, 1960) teaches the use of certain dihydrocarbon polysiloxane oils having a hydrocarbon substituent to silicon aton ratio of 1.6 to 2.0, preferably from 1.889 to 2.0 and an average of from 1 to 2 preferably from 1 to 1.5, lower alkoxy groups, per terminal silicon atom to improve the bin-aging characteristics of filler-containing polydiorganosiloxane gum compositions. Ethoxy radicals appear to be the alkoxy radical of choice and the polysiloxane oils used in these compositions contain at least 4 and as much as 35 or more dihydrocarbonsiloxy units per molecule and have molecular weights of from about 400 to 2700, preferably from about 600 to 1500. The method of preparing such polysiloxane oils is said to be taught in U.S. Pat. No. 2,909,549 (Bailey, issued Oct. 20, 1959) which teaches that alkoxy-endblocked polysiloxanes can be produced by equilibrating, among other reactants, monoalkyltrialkoxysilanes or dialkyldialkoxysilanes with cyclic polysiloxanes in the presence of a basic catalyst.

U.S. Pat. No. 3,024,126 (Brown, issued Mar. 6, 1962) teaches that reinforcing silica fillers can be surface-treated with certain hydroxy or alkoxy functional organosilanes in an organic solvent in the presence of certain basic catalysts. The Brown Patent teaches the use of certain lower molecular weight monoalkoxy- and dialkoxy-endblocked dihydrocarbonsiloxanes as surface treating agents, but teaches that there should not be more than three and preferably no more than one aliphatic, monovalent hydrocarbon radical per siloxane unit. If more than about three di-aliphatic-monovalent-hydrocarbon-radical-substituted silicon atoms in any siloxane molecule, the Brown Patent teaches that the effectiveness of the resulting treated silica will be substantially reduced.

U.S. Pat. No. 3,979,546 (Lewis, issued Sept. 7, 1976) teaches the surfaces of inorganic materials can be rendered hydrophobic by contacting them with alpha-alkoxy-omegasiloxanols containing one alkoxy group per molecule which are obtained from the reaction of cyclic siloxanes which alcohols under mild reaction conditions. While reasonably rapid conversion to product is obtained from hexamethylcyclotrisiloxane, Examples 3 and 4 indicate that conversion of octamethylcyclotetrasiloxane and decamethylcyclopentasiloxane to the corresponding alpha-alkoxy, omega-siloxanol useful as a treating agent was rather slow.

U.S. Pat. No. 2,927,909 (Lyons, et al., issued Mar. 8, 1960) teaches the use of (A) 65–85 parts by weight of a copolymer of 65–85 mole percent of monomethylsiloxane, 15–30 mole percent of dimethylsiloxane and no more than 5 mole percent of trimethylsiloxane which has from 1–12 weight percent silicon-bonded methoxy radicals and (B) from 15–35 parts by weight of monopropylsiloxane containing from 15 to 60% by weight silicon-bonded ethoxy radicals as a masonry water repellent. Nothing is taught concerning the use of component (A) and/or (B) to surface treat inorganic particulate fillers.

U.S. Pat. No. 2,706,724 (Bass, issued Apr. 19, 1955) teaches the use of a partial hydrolyzate of an alkoxylated (20–50 weight percent alkoxy radicals) mixture of by-product chlorosilicon compounds obtained from the reaction of $CH_3Cl$ and Si as a water repellent treatment for masonry. Nothing is taught concerning the use of the compositions described in the Bass Patent for surface-treating inorganic particulate fillers.

SUMMARY OF THE INVENTION

It has been discovered that a unique equilibrated reaction mixture consisting of a mixture of certain methoxy-functional organosilanes and organosiloxanes having an overall average molecular weight of less than 500 can be employed to surface-treat particulate inorganic fillers, particularly reinforcing siliceous fillers, at room temperature or above. The equilibrated reaction mixture is preferably obtained by equilibrating a mixture of $RSi(OCH_3)_3$ with a mixture of cyclic diorganosiloxanes consisting predominantly of readily commercially available liquid diorganocyclotetrasiloxanes which tend to be much less reactive to ring opening reactions than are the diorganocyclotrisiloxanes such as hexamethylcyclotrisiloxane which is a waxy solid at room temperature.

Inorganic particulate fillers, particularly reinforcing silica fillers, can be used to produce compositions curable to silicone elastomers which are easier to handle and extrude in the uncured state. The uncured compositions can be stored for periods of several weeks to several months without developing a sufficient amount of structure build-up to become crepe-hardened. Furthermore, the equilibrated reaction mixtures employed in the method of the present invention enable one to produce surface-treated, hydrophobic reinforcing silica fillers which can be used to produce cured silicone elastomers which are optically clear and possess tensile strength, elongation at break, durometer and tear values which make cured elastomers containing such treated fillers uniquely suitable for articles such as rubber tubing, windshield interlayers, and when the cured elastomer is biocompatible, for use as elastomeric prosthetic devices such as eye contact lenses, implantable devices such as mammary implants, finger joints and other devices designed for use on or within the body.

DETAILED DESCRIPTION OF THE INVENTION

The present invention relates to a method of surface treating a particulate inorganic filler which comprises the steps of (A) contacting 100 parts by weight of a particulate inorganic filler with a surface treating agent comprising at least one component which is an equilibrated reaction mixture consisting essentially of $R_2Si$-

$O_{2/2}$ units, $RSiO_{3/2}$ units and $CH_3O_{1/2}$ radicals, there being A moles of $R_2SiO_{2/2}$ units per mole of $RSiO_{3/2}$ units present in said mixture and B moles of said $CH_3O_{1/2}$ radicals, said A having an average value of from 0.5 to 10 and B having an average value of from 3 to 6, the value of B being related to A such that when $A=0.5$, $B=6$ and when $A=10$, $B=3$, and wherein R is selected from the group consisting of hydrocarbon radicals of from 1 to 10 inclusive carbon atoms and haloalkyl radicals of from 1 to 10 inclusive carbon atoms, there being at least 5 parts by weight of said equilibrated reaction mixture based on the total weight of $R_2SiO_{2/2}$ and $RSiO_{3/2}$ units present in the mixture per 100 parts by weight of said filler, and (B) maintaining said surface-treating agent in contact with said filler for a sufficient amount of time to obtain a hydrophobic, surface-treated particulate inorganic filler.

This invention also relates to the surface-treated fillers themselves and to compositions curable to silicone elastomers which contain inorganic particulate fillers surface treated by the above method. This invention also relates to cured silicone elastomers containing inorganic particulate fillers which are surface treated by the above method and more particularly to cured silicone elastomers in the form of prosthetic devices.

Examples of inorganic particulate fillers useful in the present invention can be any of a number of well-known fillers used to formulate silicone elastomers such as finely divided pure silicas such as those obtained by the flame hydrolysis of silanes sold under the trademarks CAB-O-SIL® and AEROSIL®, precipitated silica fillers prepared from sodium silicate or alkyl orthosilicates, diatomaceous silica, aluminum silicate, calcium carbonate, zinc oxide, zirconium silicate, titanium dioxide, barium sulfate, aluminum oxide, powdered quartz and the like. Preferably, reinforcing silia fillers such as fume silica or precipitated silica having B.E.T. (Brunauer, Emmett and Teller) Method surface areas of at least 50 square meters per gram and preferably greater than 200 square meters per gram are used.

The equilibrated reaction mixture consists essentially of the product of an equilibrium reaction between a source of $R_2SiO_{2/2}$ units which is preferably at least one cyclic polydiorganosiloxane of the unit formula $(R_1SiO)_x$ wherein x has a value of from 3 to 7 and an organosilane of the formula $RSi(OCH_3)_3$. Preferably, the source of $R_2SiO_{2/2}$ units is a mixture of cyclic polydiorganosiloxanes of the unit formula $(R_2SiO)_x$ wherein at least 70 weight percent of the mixture is composed of cyclic polydiorganosiloxanes wherein $x=4$ since, as is well known in the art, such a mixture is readily obtained from the hydrolysis of dimethyldichlorosilanes. The use of a methoxy-functional organosiloxane is preferred because the methoxy radical rapidly reacts with, for example, hydroxyl groups present on the surface of inorganic fillers, especially those on siliceous fillers, to produce a low molecular weight alcohol (methanol) and also has the advantage of providing the highest level of treatment efficiency due to the low molecular weight of the methoxy radical relative to the remainder of the siloxane units present in the reaction mixture. Each R is selected from the group consisting of hydrocarbon radicals of from 1 to 10 inclusive carbon atoms such as methyl, ethyl, propyl, hexyl, cyclohexyl, phenyl, benzyl, vinyl, allyl and naphthyl, haloalkyl radicals of from 1 to 10 inclusive carbon atoms such as chloromethyl, 3,3,3-trifluoropropyl and $CF_3C_9H_{18}$—, with R preferably being methyl, vinyl, phenyl and 3,3,3-trifluoropropyl radicals since organosilanes and organosiloxanes bearing those radicals are commonly available and is, more preferably, methyl and vinyl radicals. Each R radical present in the equilibrated reaction mixture can be the same or different, but, preferably, more than 50 mole percent of the R radicals, and, more preferably, at least 90 mole percent of the R radicals present in the equilibrated reaction mixture are methyl radicals since materials bearing such radicals are commercially available materials.

A sufficient amount of the source of $R_2SiO_{2/2}$ units and organosilioxane, $RSi(OCH_3)_3$ to result in a molar ratio of $R_2SiO_{2/2}$ units to $RSiO_{3/2}$ units ($R_2SiO_{2/2}:RSiO_{3/2}$) in the range of 0.5:1 to 10:1 are equilibrated at a temperature from about 40° C. to 200° C. for a period of several minutes to several days in the presence of an acidic or basic catalyst substantially in the absence of water (or at least provided with a well known means to remove any water that might be generated during the equilibration reaction, e.g., by azeotropically removing the water). Equilibration techniques for preparing such mixtures are well known in the art and further details concerning the preparation of such mixtures will be given in the following Examples. Generally, a basic catalyst such as potassium silanolate present in a ratio of 1 potassium atom per 1000 to 5000 silicon atoms present in the mixture gave equilibrated reaction mixtures within less than about 3 hours at 95°–120° C. The progress of the equilibration reaction is followed by observing the eluted fractions through the use of gas-liquid chromatographic techniques. The reaction mixture is considered to be "equilibrated" for the purposes of this invention when the eluted fractions found in a gas-liquid chromatogram of the reaction mixture shows that the composition of the reaction mixture attained relatively constant composition. After equilibration, the overall composition of the equilibrated mixture "consists essentially" of $R_2SiO_{2/2}$ units, $RSiO_{3/2}$ units and $CH_3O_{1/2}$ radicals, there being A moles of $R_2SiO_{2/2}$ units per mole of $RSiO_{3/2}$ units present in said mixture and B moles of said $CH_3O_{1/2}$ radicals, said A having an average value of 0.5 to 10 and B having an average value of from 3 to 6, the value of B is dependent upon the value of A with $B=6$ when $A=0.5$ and $B=3$ when $A=10$.

The lowest average molecular weight equilibrated reaction mixtures are obtained when 0.5 moles of $R_2SiO_{2/2}$ units is equilibrated with 1 mole of $RSi(OCH_3)_3$ and that ratio is about the lower limit for obtaining efficient filler surface-treatment. The highest average molecular weight equilibrated reaction mixtures are obtained when 10 moles of $R_2SiO_{2/2}$ units are equilibrated with 1 mole of $RSi(OCH_3)_3$ units. This ratio was deemed to be the upper limit for efficient surface-treatment because as the molar ratio of $R_2SiO_{2/2}:RSiO_{3/2}$ of the equilibrated reaction mixture was increased, longer periods of time were required to surface-treat silica filler particles at room temperature as evidenced (see the following Examples) by the amount of filler aging time necessary to obtain ultimate physical properties when cured silicone elastomers were prepared using silica fillers treated in accordance with the method of the present invention. It was unexpectedly found that the most desirable balance of uncured silicone elastomer plasticity and handling properties coupled with high optical clarity and physical properties such as a combination of a high tensile strength with relatively high elongation and Die B tear values was obtained when the reaction mixtures employed to surface treat the silica filler had molar ratios of $R_2SiO_{2/2}:RSiO_{3/2}$ in the range of 0.75 to 4 and the best overall balance of properties was obtained when the ratio was between 0.9 and 1.1. This is unexpected since a 1:1 molar ratio indicates that about 50 mole percent of the surface-treating agent is composed of $RSiO_{3/2}$ units. It has been more common to employ surface-treating agents for siliceous and other fillers which are predominantly composed of $R_2SiO_{2/2}$ units or triorganosiloxy units such as those derived from hexamethyldisilazane. The latter agents have a higher number of R radicals per siloxane unit and would be expected to more efficiently surface-treat and render the surface of fillers hydrophobic than would $RSiO_{3/2}$ units.

Examples of sources of $R_2SiO_{2/2}$ units are the previously mentioned cyclic polysiloxanes which are preferred because they add no other potentially hydrolyzable groups to the reaction mixture. More specifically, cyclic polydimethyl siloxane such as hexamethylcyclotrisiloxane, octamethylcyclotetrasiloxane, decamethylcyclopentasiloxane, $[(C_6H_5)_2SiO]_3$, 1,3,5-trimethyl-1,3,5-trivinylcyclotrisiloxane, 1,3,5-trimethyl-1,3,5-tris(3,3,3-trifluoropropyl)-cyclotrisiloxane, mixtures of cyclic ploydiorganosiloxanes, and, when an economical source of $R_2SiO_{2/2}$ units is desired, especially when R is a methyl radical, preferably a mixture of cyclic polydimethylisiloxanes of the unit formula $(R_2SiO)_x$ is used wherein at least 70 weight percent of the mixture is composed of cyclic polydiorganosiloxanes wherein x=4. The term "consisting essentially of" with reference to the equilibrated reaction mixtures useful in the method of the present invention is intended to mean that a small amount of other siloxane units, in any event no more than 5 mole percent of the total siloxane units present in the equilibrated reaction mixture, can be units such as $R_3SiO_{0.5}$ that could be present if a low molecular weight triorganosiloxy-endblocked polydiorganosiloxane fluid such as $(CH_3)_3SiO[(CH_3)_2SiO]_ySi(CH_3)_3$ where y has an average value of from 1 to 10 were used as a source for the $R_2SiO_{2/2}$ units, however the previously mentioned cyclic polydiorganosiloxanes are preferred.

Specific examples of $RSi(OCH_3)_3$ are methyltrimethoxysilane, ethyltrimethoxysilane, phenyltrimethoxysilane, vinyltrimethoxysilane, allyltrimethoxysilane, chloromethyltrimethoxysilane and 3,3,3-trifluoropropyltrimethoxysilane, with methyltrimethoxysilane and vinyltrimethoxysilane being preferred.

One advantage of using the equilibrated reaction mixtures of the present invention is that if necessary, the equilibration catalyst is simply removed from the equilibrated reaction mixture and the reaction mixture is stored in the absence of moisture until it is used, as is, to surface treat a particulate inorganic solid. There is no need to use a stripping process to remove any of the components of the mixture before use.

The inorganic particulate filler can be surface treated with the above equilibrated reaction mixtures themselves simply by bringing the equilibrated reaction mixture into intimate contact with the filler itself or by blending the filler to be treated into at least one polydiorganosiloxane and thereafter introducing an amount of the equilibrated reaction mixture into the filler-polydiorganosiloxane composition. Generally, about 5 parts by weight of the equilibrated reaction mixture (calculated as a total weight of $R_2SiO_{2/2}$ and $RSiO_{3/2}$) per 100 parts by weight of the filler to be treated is necessary to provide the filler with an adequate level of surface-treatment to enable it to become surface treated and hydrophobic and to improve the physical properties of the silicone elastomer compositions into which it is added. While there is no critical upper limit for the amount of equilibrated reaction mixture (calculated as a totoal weight of $R_2SiO_{2/2}$ and $RSiO_{3/2}$) used to surface treat the filler, the use of a sufficient amount of equilibrated reaction mixture to provide more than about 50 parts by weight of total $R_2SiO_{2/2}$ and $RSiO_{3/2}$ units per 100 parts by weight of filler may be wasteful and can have a detrimental effect on the properties of cured elastomers containing such fillers. The actual surface treating agent employed in the method of the present invention may include more than just the equilibrated reaction mixture as will be shown in the following Examples. For example, a basic catalyst such as ammonium hydroxide or ammonium carbonate can be used to improve the filler surface treatment rate. The equilibrated reaction mixture can also be dissolved in an organic solvent such as methanol or toluene, which optionally includes a basic catalyst, and used to surface treat the filler in a solvent slurry. The fillers are then aged for a sufficient amount of time at room temperature up to about 100° C., preferably at room temperature, until the fillers become hydrophobic and surface treated, generally from about 15 minutes to several weeks, preferably from 15 minutes to 24 hours and most preferably from 15 minutes to 4 hours. Hydrophobic reinforcing silica fillers prepared by precipitating alkyl silicates of the type described in U.S. Pat. No. 4,344,800 (Lutz, issued Aug. 17, 1982) can be produced by substituting the equilibrated reaction mixtures of the present invention in place of the hydrophobe agents described in the Lutz Patent and that patent is hereby incorporated by reference to teach another method by which the method of the present invention can be practiced. Other methods of surface treating particulate fillers in accordance with the method of the present invention will be evident to those skilled in the art. Several silica fillers prepared by substituting the equilibrated reaction mixtures of the present invention for the hydrophobe agents described in the Lutz Patent were found to have BET surface areas of from 290 to 330 $m^2/g$.

The surface-treated fillers obtained by the above method can then be compounded into polydiorganosiloxanes to form compositions curable to silicone elastomers using polydiorganosiloxanes and compounding methods which will be familiar to those skilled in the art. Polydiorganosiloxanes useful in preparing compositions curable to silicone elastomers are well known and the nature of the polydiorganosiloxanes into which surface-treated inorganic particulate fillers, particularly surface treated reinforcing siliceous fillers, of the present invention are compounded forms no part of the present invention. Generally, the compositions curable to silicone elastomers comprise from 50 to 97.5 parts by weight of at least one polydiorganosiloxane and from 2.5 to 50 parts by weight of surface-treated particulate inorganic filler. One type of curable composition employing surface-treated silica fillers is described in pending U.S. patent application Ser. No. 309,302, filed on Oct. 7, 1981 (now U.S. Pat. No. 4,418,165) in the names of K. E. Polmanteer and H. L. Chapman entitled "Optically Clear Silicone Compositions Curable to Elastomers" which is assigned to the same assignee as is the present invention. U.S. Ser. No. 309,302 above is hereby incorporated by reference to teach polydiorganosiloxanes which can be used in combination with the surface-treated silica fillers of the present invention to prepare cured silicone elastomers possessing high optical clarity, to teach methods for incorporating such fillers into the polydiorganosiloxanes and to teach methods for curing such compositions. Other examples of patents describing polydiorganosiloxanes curable to silicone elastomers are those patents listed in U.S. Pat. No. 3,677,877 (Metevia, et al., issued July 18, 1972) which are hereby incorporated by reference to teach such polydiorganosiloxanes, curable compositions containing such polydiorganosiloxanes and methods of curing the same.

Cured silicone elastomers containing surface-treated inorganic particulate fillers of the present invention are useful in various applications such as molded articles in the form of hoses, gaskets and, face masks. Cured polydimethylsiloxane elastomers containing reinforcing siliceous fillers of the present invention, particularly those made from the alkaline hydrolysis of methyl orthosilicate, were found to possess high optical clarity in addition to a combination of high tensile strength, high elongation and reasonably high durometer and Die B tear values which makes such cured elastomers highly desirable for use as prosthetic devices for use or in combination with the body such as eye contact lenses, implantable devices such as finger joints, mammary prostheses, chin implants and the like.

The following definitions shall apply in the Examples below:

"Me"—Methyl.

"Vi"—Vinyl.

"MTMS"—Methyltrimethoxysilane

"Mixed Cyclics"—A mixture of cyclic polydimethylsiloxanes of the unit formula $[(CH_3)_2SiO]_x$ where x has an integral value of from 3 to 7 and wherein about 78 weight percent of the mixture is composed of $[(CH_3)_2SiO]_4$.

"Conc. Ammonium Hydroxide"—Concentrated aqueous ammonium hydroxide having approximately 28% $NH_3$ content and a density of approximately 0.9 g/ml where "g" is grams and "ml" is milliliters.

"$NH_3$/Methanol Solution"—Solution of ammonia gas in methanol containing approximately 0.11 g $NH_3$/ml, density approximately 0.8 g/ml.

"MOS"—Methyl orthosilicate (density approximately 1.014 g/ml).

"Catalyst A"—Hexane solution of a potassium silanolate catalyst having a basic neutralization equivalent of 2700 g/equivalent of potassium.

"Catalyst B"—Ion exchange resin in bead form bearing surface-bonded sulfonic acid groups which is sold under the trademark "AMBERLYST®15" by Rohm and Haas Company, Inc., Philadelphia, PA.

"Catalyst C"—Potassium silanolate catalyst having a neutralization equivalent of 425 g/equivalent of potassium.

"Gum A"—A dimethylvinylsiloxy-endblocked polydiorganosiloxane gum consisting essentially of 99.86 mole percent of dimethylsiloxane units and 0.14 mole percent of methylvinylsiloxane units based on the total moles of diorganosiloxane units present and having a plasticity (4.2 g sample) in the range of about 1.40–1.65 millimeters (55–65 mils).

"Peroxide A"—2,5-dimethyl-2,5-di(t-butylperoxy)-hexane.

The test methods used in the following Examples are as follows:

Water Flotation Test (Hydrophobicity of Fillers)—A sample of the silica filler to be tested is dried in an oven for 15 minutes at 200° C. Approximately 0.1 g of the dried filler (pulverized to insure that it is free of large particles) is added to 10 ml water in a vial (1 oz. (30 ml) volume). The vial is capped and vigorously shaken for about one minute. After shaking, the amount of powdered sample that floated on the top of the water was visually estimated. If all of the dried silica powder floated at the top, the sample was deemed to possess 100% Hydrophobicity according to the test.

Filler Nonvolatile Solids Content—A sample of filler (10–20 g wet, gelled filler for Examples 1–7, about 2–3 grams for Example 8) is weighed by difference into a weighing dish, dried for 2 hours at 150° C. and reweighed. The final weight divided by the intial weight is reported as percent nonvolatile solids content.

Treating Agent Level—For purpose of calculation, it is assumed that no methanol or other volatile materials are lost during the equilibration step. The level of filler treating agent desired (based upon the total weight of the surface-treated filler) is calculated. The amount of reaction mixture needed to provide the desired weight of a product (nonvolatile surface-treating moeities) consisting of $R_2SiO_{2/2}$ units and $RSiO_{3/2}$ units in the desired ratio is then calculated and that amount of reaction mixture is used to treat the filler. For example, an equilibrated reaction mixture obtained by equilibrating 136.1 g (1 mole) methyltrimethoxysilane with 74 g (1 mole of $(CH_3)_2SiO_{2/2}$ units) of cyclic polysiloxanes of the unit formula $[(CH_3)_2SiO]_x$ where x=3 to 7 would have a total weight of 136.1 g+74 g=210.1 g and would provide 67.1 g of $CH_3SiO_{3/2}$ units and 74 g of $(CH_3)_2SiO_{2/2}$ units for a total of 141.1 g of nonvolatile surface-treating moeities. Thus, assuming that the filler will accept 40 weight percent of surface-treatment moieties, 100 g of a silica $(SiO_2)$ filler would require $(0.40\times100$ g)$\div0.60=66.7$ g of nonvolatile surface treating moieties or $(210.1$ g$\times66.7)\div141.1=99.3$ g of the equilibrated reaction mixture.

The plasticity of the uncured elastomer formulation or the unfilled gum was measured using a procedure based on that outlined in ASTM D926. A sample weighing either twice the specific gravity (in grams) of material containing a filler or four times the specific gravity (in grams) of unfilled gum is cut from the larger mass of material and rolled into a ball. The material, in the shape of a ball, was then allowed to age for one hour at 23°±1° C. The sample was then placed between the platens of a plastometer (Catalog No. C 544445 Parallel Plate Plastometer, Scott Tester, Inc., Providence, R.I.) and the upper plate was lowered until it just touched the top of the sample and was then released without dropping it. The plasticity reported is the thickness of the sample 3 minutes ±5 seconds after the release of the upper platen when the sample is at 23°±1° C. The physical properties of the cured and/or post-cured silicone rubbers were obtained using the following ASTM Methods: ASTM D412—ultimate tensile strength (tensile stress), elongation at break and modulus (or tensile stress) at 100% elongation: ASTM D624—tear (Die B); and ASTM D2240—durometer. The procedure followed to obtain the haze and luminous transmittance values is set out in ASTM D1003-61 and were done on samples that were nominally 1.52 mm (60 mil) thick. The instrument used to obtain the values reported in the following examples was a Gardner Pivotable Sphere Hazemeter (Model HG 1024) equipped with a Model PG 5500 Digital Photometer (Gardner Laboratory, Bethesda, MD 20014). CIE Source C, sometimes called Illuminant C, was used in measuring the above values. The haze value reported is percent haze per 1.52 mm (60 mil) thickness.

The following examples are intended as being merely illustrative and are not to be construed as limiting the scope of the present invention to those examples alone. The scope of the invention is properly defined by the appended claims. All parts and percentages reported in the following examples are by weight unless otherwise indicated.

EXAMPLE 1

This Example demonstrates the preparation of equilibrated reaction mixtures useful in the present invention and their use as surface-treating agents in the preparation of a hydrophobic reinforcing silica filler. Five mixtures of Mixed Cyclics and methyltrimethoxysilane (MTMS) (see Table I for the reactants) were equilibrated in the presence of a sufficient amount of Catalyst A to provide 1 potassium atom per 1000 silicon atoms (1K/1000Si) present in the mixture.

The equilibration of each mixture was carried out in the absence of moisture at 40° C. for a period of 5 days to insure that each mixture was fully equilibrated (see Example 2 for the type of apparatus used). The composition of each reaction mixture was monitored daily by means of gas-liquid chromatography. After 5 days, the gas-liquid chromatogram obtained after 4 and 5 days, respectively, for each reaction mixture were substantially the same and all samples were then deemed to be "equilibrated". Each equilibrated reaction mixture was then cooled to room temperature. The potassium catalyst was neutralized and precipitated from the reaction mixture by adding an appropriate amount of dry ice (frozen carbon dioxide) to each reaction mixture. Each equilibrated reaction mixture was filtered through a bed of perlite filtering aid supported on a medium porosity glass frit and the filtrates (Reaction Mixtures A-E, respectively) were stored in the absence of moisture until each was used to surface treat a silica filler as follows.

A hydrophobic reinforcing silica filler was prepared as described in U.S. Pat. No. 4,344,800 for each Reaction Mixture by first preparing a solution of 7.9 ml methanol, 3.2 ml $NH_3$/Methanol Solution and 2.7 ml Conc. Ammonium Hydroxide at room temperature. Then, the number of grams of each Reaction Mixture indicated in Table II was added, with stirring, to that solution. Shortly thereafter, 7.2 ml MOS was added to the stirring mixture. Stirring was continued until the mixture gelled (less than 2 minutes) and formed a silica filler-containing composition. The filler-containing composition was allowed to age at room temperature. Using the gelation point as the starting point, samples of filler-containing composition were withdrawn at the intervals indicated in Table II and tested for hydrophobicity using the Water-Flotation Test. The amounts of each Reaction Mixture decrease as the Molar Ratio of $R_2SiO_{2/2}$:$RSiO_{3/2}$ increases to obtain a similar level of surface-treatment on each sample of filler. The results are reported in Table II. For this series, Reaction Mixtures A and B became 100% hydrophobic in the shortest period of time.

TABLE I

| Reaction Mixture | Mixed Cyclics g(moles[1]) | MTMS g(moles[2]) | Molar Ratio[3] $Me_2SiO_{2/2}$:$MeSiO_{3/2}$ |
|---|---|---|---|
| A | 2.5(0.035) | 4.7(0.035) | 1:1 |
| B | 3.1(0.04) | 2.7(0.02) | 2:1 |
| C | 3.6(0.05) | 1.6(0.012) | 4.2:1 |
| D | 3.6(0.05) | 0.9(0.007) | 6.9:1 |
| E | 3.7(0.05) | 0.7(0.005) | 10:1 |

[1]Moles of $Me_2SiO_{2/2}$
[2]Moles of $MeSiO_{3/2}$
[3]$Me_2SiO_{2/2}$:$MeSiO_{3/2}$

TABLE II

| Run No. | 1 | 2 | 3 | 4 | 5 |
|---|---|---|---|---|---|
| Reaction Mixture | A | B | C | D | E |
| Amount of Reaction Mixture (g) | 3.4 | 2.9 | 2.6 | 2.3 | 2.2 |
| Molar Ratio[2] | 1:1 | 2:1 | 4.2:1 | 6.9:1 | 10:1 |
| % HYDROPHOBICITY | | | | | |
| Time (minutes): | | | | | |
| 15 | 50 | 100 | 40 | 20 | 15 |
| 45 | 100 | 100 | 75 | 50 | 25 |
| 60 | 100 | 100 | 90 | 80 | 50 |
| 120 | 100 | 100 | 100 | 90 | 60 |
| 180 | 100[2] | 100[2] | 100 | 95 | 90 |
| 240 | — | — | 100[2] | 98 | 98 |
| 300 | — | — | — | 100 | 100 |

[1]Ratio of $Me_2SiO_{2/2}$:$MeSiO_{3/2}$
[2]Filler sample tended to crawl up side of vial

EXAMPLE 2

This Example describes the production of hydrophobic reinforcing silica fillers using surface-treating agents derived from reaction mixtures that were equilibrated with a basic catalyst or with an acidic catalyst.

Reaction Mixture F was prepared in the absence of moisture in a manner similar to that employed in Example 1. A higher reaction temperature was used to reduce the time needed to reach an equilibrated mixture. Thus, 544 g of MTMS, 296 g of Mixed Cyclics and 21.6 g of Catalyst A were combined, with stirring, in a round bottom flask equipped with an air-driven stirrer, water-cooled condenser fitted with a drying tube, thermometer and an addition funnel. After all three components were added, the contents of the flask were heated to 100° C., maintained at 100° C. for 30 minutes and then cooled to room temperature. As in Example 1, the catalyst was neutralized and the contents were filtered to obtain equilibrated Reaction Mixture F. A gas-liquid chromatogram of equilibrated Reaction Mixture F showed that it had reached substantially an equilibrium level of eluted fractions based upon previous experiences with reaction mixtures having a molar ratio of $Me_2SiO_{2/2}$:$MeSiO_{3/2}$ of 1:1.

Reaction Mixture G was prepared using an equilibration procedure employing an acidic catalyst on a solid resinous support medium. To remove any free acid that might be present, Catalyst B was thoroughly washed with methanol until the decanted methanol was neutral when tested with pH indicator paper. The residual methanol was then removed via vacuum filtration and the Catalyst B was dried for 1 hour at 40° C. before it was used. A vacuum-jacketed, glass column (2 cm inner diameter) having a stopcock at its lower end was packed with washed beads of Catalyst B to a depth of 45.7 cm (18 inches) and the bottom of the column attached to a 3-liter, round-bottom flask fitted with a water-cooled condenser. A 3-liter, round-bottomed flask having a bottom drain, an air-powered stirrer, thermometer and water-cooled condenser was attached to the top of the column by means of the bottom drain. The top flask was filled with an equimolar mixture of MTMS and Mixed Cyclics and the contents were heated to 95° C. with stirring. A sufficient amount of the contents (at 95° C.) was introduced into the catalyst column to fill the column and allowed to remain there for 15 minutes to warm the catalyst beads. This was then drained and the remaining contents of the flask (at 95° C.) was allowed to flow through the column into the lower flask at the rate of 17 g/minute. A gas-liquid chromatogram of the contents of the lower flask (Reaction Mixture G) showed that the reaction mixture was substantially equilibrated and contained substantially the same levels of eluted fractions as were exhibited by Reaction Mixture F.

Hydrophobic reinforcing silica fillers were prepared as in Example 1 using the following formulations. Filler F: 82 ml methanol, 31.9 ml NH$_3$/Methanol Solution, 28.2 ml Conc. Ammonium Hydroxide, 29.65 g Reaction Mixture F and 75 ml MOS. The wet, gelled filler composition containing Filler F contained 23.3% nonvolatile solids content and was aged for at least 24 hours to insure that the filler was adequately surface-treated before it was compounded into a polysiloxane gum (elastomer composition). Then 66.6 g of the wet, gelled filler composition containing about 15 g Filler F was added to 25 g of Gum A on a two-roll mill without the application of any external heating. After all of the filler composition was added, the filler-gum base was heated to 120° C. and hot-milled for 15 minutes to remove the volatile portion of the filler composition. The base was then cooled to room temperature and 13 drops of Peroxide A (0.7 parts by weight per 100 parts by weight of Gum A) was milled into the base. The catalyzed base was then placed between two sheets of precision calendered polytetrafluoroethylene films in a square molding chase having polished mold surfaces to prepare a cured elastomer sample with a nominal thickness of 1.52 mm (60 mils). The chase was placed in a molding press and the catalyzed base was cured for 15 minutes at 170° C. followed by a post cure out of the mold for 1 hour at 200° C. The cured elastomer was aged overnight at room temperature and its physical properties were then tested. Unless otherwise indicated, this procedure was used to cure and test the compositions described in this and the following Examples.

A hydrophobic reinforcing silica filler (Filler G) was prepared with Reaction Mixture G in place of Reaction Mixture F using the same ratios of ingredients as described above. The resulting wet, gelled filler composition containing Filler G had a nonvolatile solids content of 23.0%. The wet, gelled filler composition was aged at least 24 hours before it was compounded into a polysiloxane gum in the same manner described above using the following formulation: 30 g Gum A, 78.3 g wet, gelled filler composition containing about 18 g Filler G and 17 drops of Peroxide A. The catalyzed base was cured in the same manner as described above.

The filler loading in each sample in parts by weight of filler (nonvolatile solids) per 100 parts by weight of polydiorganosiloxane (hereinafter referred to as "phr") was 62 phr for Run 6 with Filler F and 60 phr for Run 7 with Filler G. Approximately 40 weight percent of each filler was calculated to be contributed by the surface-treating agent. The physical properties of the cured elastomer are reported in Table III.

TABLE III

| Run No.<br>Filler in Sample | 6<br>Filler F | 7<br>Filler G |
|---|---|---|
| Physical Properties: | | |
| Tensile Strength (MPa/psi)[1] | 12.4/1800 | 12.1/1760 |
| Elongation at Break (%) | 630 | 600 |
| Modulus, 100% Elongation (MPa/psi) | 1.45/210 | 1.38/200 |
| Durometer (Shore A) | 56 | 56 |
| Tear, Die B (kN/m/(ppi))[2] | 23.6/135 | 22.8/130 |
| Haze Value | 3.1 | 4.2 |

[1]MPa is megapascals - 6.895 MPa = 1000 pounds per square inch (psi)
[2]kN/m is kilonewtons per meter - 175 kN/m = 1000 pounds per inch (ppi)

The physical properties for Runs 6 and 7 are quite similar, thus showing that acid or base catalysis can be employed to obtain the equilibrated reaction mixtures useful in the present invention.

EXAMPLE 3

This Example illustrates the effect of varying the molar ratio of Me$_2$SiO$_{2/2}$:MeSiO$_{3/2}$ on the physical properties of the cured elastomers. The Fillers employed in Runs 8 and 9 were prepared using a 40 weight percent surface treating agent level for each of the Reaction Mixtures shown in Table IV. The same ratios of ingredients were employed to make the wet, gelled fillers used in these Runs as were used in Example 2 for Filler F. Each wet, gelled filler composition was aged for 4 hours at room temperature before each was compounded into a composition curable to an elastomer using the same ratios of ingredients and curing procedure as described for Example 2 above. The physical properties of the cured elastomers are reported in Table IV below. Run 10 was prepared in the same manner as were Runs 8 and 9 using the following formulation: 60 ml methanol, 22.6 ml NH$_3$/Methanol Solution, 20.6 g equilibrated reaction mixture, 20.4 ml Conc. Ammonium Hydroxide and 54 ml MOS. Runs 11 and 12 were the same filler formulations as were used in Runs 8 and 9, respectively, but the fillers were allowed to age 24 hours at room temperature before compounding into elastomers. Run 13 employed the same filler ingredient ratios as in Runs 8 and 9, but the filler was aged overnight (about 16 hours) before it was compounded and cured as in Runs 8 and 9. Aging the fillers enables the fillers to become more completely surface-treated and physical properties such as haze value, tear and elongation at break generally improve with aging as can be seen from Table IV.

TABLE IV

| Run No. | 8 | 9 | 10 |
|---|---|---|---|
| Equil. Reaction Mixture: | | | |
| Me$_2$SiO$_{2/2}$:MeSiO$_{3/2}$ | 1:1 | 4:1 | 10:1 |
| Filler Aging Time (hours) | 4 | 4 | 4 |
| Physical Properties: | | | |
| Tensile Strength (MPa/psi) | 12.3/1790 | 10.2/1480 | 7.6/1100 |
| Elongation at Break (%) | 540 | 550 | 580 |
| Modulus, 100% Elong. (MPa/psi) | 1.65/240 | 1.52/220 | — |
| Durometer (Shore A) | 60 | 63 | 63 |
| Tear, Die B (kN/m/(ppi)) | 19.8/113 | 19.3/110 | 16.8/96 |
| Haze Value | 4.5 | 5.3 | 15.5 |
| Plasticity/Recovery | 188/12 | 212/10 | —/— |
| Run No. | 11 | 12 | 13 |
| Equil. Reaction Mixture: | | | |
| Me$_2$SiO$_{2/2}$:MeSiO$_{3/2}$ | 1:1 | 1:4 | 1:2.5 |

TABLE IV-continued

| Filler Aging Time (hours) | 24 | 24 | 16 |
|---|---|---|---|
| Physical Properties: | | | |
| Tensile Strength (MPa/psi) | 11.2/1620 | 11.0/1600 | 9.65/1400 |
| Elongation at Break (%) | 625 | 550 | 680 |
| Modulus, 100% Elong. (MPa/psi) | 1.10/160 | 1.38/200 | 1.10/160 |
| Durometer (Shore A) | 53 | 60 | 48 |
| Tear, Die B (kN/m/(ppi)) | 24.5/140 | 24.8/142 | 21.8/125 |
| Haze Value | 1.7 | 3.7 | 4.1 |
| Plasticity/Recovery | 138/11 | 197/10 | —/— |

EXAMPLE 4

This Example describes the use of equilibrated reaction mixtures containing siloxane units bearing silicon-bonded hydrocarbon radicals such as phenyl, vinyl and 3,3,3-trifluoropropyl radicals in addition to methyl radicals.

Equilibrated Reaction Mixture H was prepared using the apparatus employed for Reaction Mixture F by equilibrating 74 g of Mixed Cyclics (1 mole of $Me_2SiO_{2/2}$ units) with a total of 39.4 g (0.2 mole) of phenyltrimethoxysilane in the presence of 0.09 g of Catalyst C (1K/5000Si). The Mixed Cyclics and one half of the phenyltrimethoxysilane was intially added to a flask and the contents heated to 120° C. At 120° C., the Catalyst C was added to the contents and, the reaction mixture was allowed to equilibrate for 45 minutes at 120° C. in the presence of the Catalyst C. Then the remainder (19.7 g) of the phenyltrimethoxysilane was added to the mixture and it was stirred another 45 minutes at 120° C. It was then cooled, neutralized and filtered as in Example 1 to obtain Reaction Mixture H. Reaction Mixture H was used to formulate Filler H according to the procedure described in Example 1 using the following ingredients: 60 ml methanol, 22.6 ml $NH_3$/Methanol Solution, 20.6 g Reaction Mixture H as a surface-treating agent, 20.4 ml Conc. Ammonium Hydroxide and 54 ml MOS.

Equilibrated Reaction Mixture I was prepared employing the apparatus used for Reaction Mixture F by equilibrating 74 g of Mixed Cyclics with a total of 29.6 g (0.2 moles) vinyltrimethoxysilane. The Mixed Cyclics and 14.8 g of vinyltrimethoxysilane were mixed together and heated to 140° C. 0.09 g (1K/5000Si) of Catalyst C was then added, the mixture was allowed to equilibrate for 15 minutes at 140° C. and then the remaining 14.8 g of vinyltrimethoxysilane was then added. After 30 minutes at 140° C., a gas-liquid chromatogram showed that the reaction mixture was substantially equilibrated and the mixture was cooled, neutralized and filtered as in Example 1 to obtain Reaction Mixture I. Filler I was prepared in the same manner as Filler H except 22.7 g Reaction Mixture I was used as the surface-treating agent in the filler formulation.

Equilibrated Reaction Mixture J was prepared using the apparatus used for Reaction Mixture F by heating 74 g Mixed Cyclics and 40.4 g (0.2 moles) 3,3,3-trifluoropropyltrimethoxysilane to 110° C. with stirring. Then 0.09 g Catalyst C (1K/5000Si) was added to the mixture and it was stirred at 110° C. for 20 minutes. At that time, the mixture was found to be substantially equilibrated via a gas-liquid chromatogram. It was cooled, neutralized and filtered as above to obtain Reaction Mixture J. Filler J was prepared in the same manner as described for Filler H using 21.3 g of Reaction Mixture J as the surface-treating agent. Each of the three wet, gelled filler compositions prepared above were allowed to age at room temperature for 4 hours (Run Nos. 14, 16 and 18) and for 3 weeks (Run Nos. 15, 17 and 19) after gelation before each was formulated into an elastomeric composition and cured according to the procedures described in Example 2. The formulation employed to make each elastomeric composition was 30 g Gum A, a sufficient amount of a wet, gelled filler composition to provide 18 g of Filler H, I or J and 0.2 g (approximately 12 drops of Peroxide A). Reaction Mixtures H, I and J all had $R_2SiO_{2/2}$:$RSiO_{3/2}$ ratios of 5:1. The physical properties obtained for the cured elastomers are reported in Table VI. Table VI indicates that filler aging (i.e., surface-treatment) time appears to have a significant effect on the optical clarity and tensile strength of the cured elastomers.

TABLE VI

| Run No. | 14 | 15 | 16 | 17 | 18 | 19 |
|---|---|---|---|---|---|---|
| Filler Type | H | H | I | I | J | J |
| Filler Aging Time | 4 hours | 3 weeks | 4 hours | 3 weeks | 4 hours | 3 weeks |
| Physical Properties: | | | | | | |
| Tensile Strength (MPa/psi) | 12.6/1830 | 9.31/1350 | 5.86/850 | 6.34/920 | 9.52/1380 | 11.4/1650 |
| Elongation at Break (%) | 610 | 550 | 50 | 60 | 550 | 550 |
| Durometer (Shore A) | 55 | 52 | 85 | 80 | 65 | 52 |
| Tear, Die B (kN/m/(ppi)) | 19.2/110 | 20.1/115 | 6.1/35 | 6.1/35 | 28.9/165 | 20.1/115 |
| Haze Value | 16.3 | 5.9 | 5.4 | 2.3 | 7.2 | 3.6 |
| Luminous Transmittance | 84.5 | 90.1 | 90.5 | 93.6 | 91.5 | 92.9 |

Reaction Mixture K was prepared using apparatus similar to that employed for Reaction Mixture F. A mixture of 136 g (1 mole) methyltrimethoxysilane, 74 g Mixed Cyclics and 3.69 g of 1,3,5-trimethyl-1,3,5-trivinylcyclotrisiloxane (0.048 moles of $MeViSiO_{2/2}$ where "Vi" is vinyl) was heated to 100° C. with stirring. At 100° C., 5.4 g of Catalyst A (1K/1000Si) was added to the mixture and it was stirred at 95°-100° C. for 45 minutes. The mixture was deemed to be substantially equilibrated at that point via a gas-liquid chromatogram and the mixture was cooled to 40° C., neutralized and filtered as above to obtain Reaction Mixture K. Filler K was prepared as above using the following formulation: 82 ml methanol, 31.9 ml $NH_3$/Methanol Solution, 28.2 ml Conc. Ammonium Hydroxide, 30.3 g Reaction Mixture K as a surface-treating agent and 75 ml MOS. The resulting wet, gelled filler composition (containing filler K) was found to have a nonvolatile solids content of 23.0% and had a calculated mole percentage of 2.1% methylvinylsiloxane units. This wet, gelled filler composition was used to prepare a cured polydimethylsiloxane silicone elastomer having a filler loading level of 60 phr which had a tensile strength value of 10.96 MPa/1590 psi, elongation at break of 917%, modulus at 100% elongation of 2.36 MPa/343 psi, durometer (Shore A) of 64, Die B tear value of 42.2 kN/m/(241 ppi), haze value of 1.6% at 1.52 mm thickness and luminous transmittance of 93.2% at 1.52 mm thickness.

Equilibrated Reaction Mixture L was prepared in the same manner as was Reaction Mixture K using 136 g (1 mole) methyltrimethoxysilane, 74 g Mixed Cyclics and 6.35 g (0.043 moles) vinyltrimethoxysilane. Filler M was prepared using the same procedure employed for Filler K using 30.7 g of Reaction Mixture L employed as the surface-treating agent. The resulting wet, gelled filler composition (22.9% nonvolatile solids content, 2.1 mole % vinylsiloxane units) containing Filler M was used to prepare a cured polydimethylsiloxane silicone elastomer having a filler loading level of 60 phr which had a tensile strength of 10.57 MPa/1533 psi, elongation at break of 787%, modulus at 100% elongation of 2.57 MPa/373 psi, durometer (Shore A) of 67, Die B tear of 41.8/kN/m/(239 ppi), haze value of 1.3% at 1.52 mm thickness and luminous transmittance of 93.3%.

EXAMPLE 5

The following wet, gelled filler composition was prepared in the manner described in Example 1 using the following formulation: 246 ml (194 g) methanol, 96 ml (76.6 g) NH$_3$/Methanol Solution, 84.6 ml (75.3 g) Conc. Ammonium Hydroxide, 89 g of an equilibrated reaction mixture having a molar ratio of Me$_2$SiO$_{2/2}$:MeSiO$_{3/2}$ units of 1:1 and 225 ml (228 g) MOS. Fillers prepared from equilibrated reaction mixtures of this molar ratio gave the best overall properties in a cured silicone elastomer in a reasonably short period of time. To demonstrate the speed at which ultimate physical properties of the cured elastomer are developed, the above wet, gelled filler composition was aged at room temperature for 1, 2, 4, 8 and 24 hours after gelation and formulated into elastomeric compositions and cured as in Example 2 using the following formulation: 25 g Gum A, 66.4 g of the wet, gelled filler composition (15 g nonvolatile solids) and 13.5 drops Peroxide A. The physical properties of the cured elastomer are reported in Table VII and the data obtained indicates that, based upon the physical properties obtained, the filler is substantially fully surface-treated after about 1 hour of aging time.

TABLE VII

| Filler Aging Time (hours) | Tensile Strength (MPa/psi) | Elong. at Break (%) | Modulus, 100% Elong. (MPa/psi) |
|---|---|---|---|
| 1 | 11.0/1600 | 570 | 1.31/190 |
| 2 | 11.0/1590 | 575 | 1.31/190 |
| 4 | 10.9/1580 | 630 | 1.03/150 |
| 8 | 11.4/1650 | 620 | 1.10/160 |
| 24 | 11.4/1660 | 620 | 1.24/180 |

| Durometer (Shore D) | Tear, Die B (kN/m/ppi)) | Haze Value | Lum. Trans. |
|---|---|---|---|
| 62 | 22.4/128 | 3.8 | 92.4 |
| 57 | 22.8/130 | 2.5 | 92.8 |
| 52 | 24.5/140 | 1.9 | 92.9 |
| 53 | 21.0/120 | 1.9 | 92.5 |
| 54 | 21.0/120 | 2.1 | 92.4 |

EXAMPLE 6

This Example illustrates the effect of filler surface treating agent level on the physical properties of cured elastomers. The fillers were prepared as in Example 1 using the ratios of ingredients shown in the following formulation: 109 ml methanol, 42.6 ml NH$_3$/Methanol Solution, 37.6 ml Conc. Ammonium Hydroxide, X g of equilibrated Reaction Mixture and 100 ml of MOS. One filler series was run using Reaction Mixture M which had a 1:1 molar ratio of Me$_2$SiO$_{2/2}$:MeSiO$_{3/2}$ wherein X in the above formulation was 19.7 g, 25.3 g, 31.6 g, 39.4 g and 48.0 g, respectively, to obtain filler surface treating agent levels of 25, 30, 35, 40 and 45 weight percent of the total filler nonvolatile content. Likewise, another filler series was run using Reaction Mixture N which had a 4:1 molar ratio of Me$_2$SiO$_{2/2}$:MeSiO$_{3/2}$ wherein X in the above formulation was 15.7 g, 20.1 g, 25.3 g, 31.4 g and 38.3 g, respectively, to obtain filler surface treating agent levels of 25, 30, 35, 40 and 45 weight percent of the total filler nonvolatile content. The fillers were then formulated into elastomer compositions using 40 g Gum A, 24 g of filler solids based on the calculated amount expected to be present in the wet, gelled filler compositions assuming 100% conversion to filler and 23 drops of Peroxide A. The fillers were aged for 4 and 24 hours, respectively, before they were formulated into the above elastomer compositions and cured as in Example I. The physical properties of the cured elastomers are reported in Table VIII for fillers treated with Reaction Mixture M and in Table IX for fillers treated with Reaction Mixture N.

The general trends observed from Tables VIII and IX are that plasticity, haze value, stress whitening, durometer and modulus values decreased upon aging while the tensile strength and elongation values increased upon aging. The fillers treated with Reaction Mixture N in general showed a greater variation in properties between 4 and 24 hours of aging time than did those using Reaction Mixture M indicating that the latter fillers appeared to be reaching an optimum level of surface treatment earlier than fillers using Reaction Mixture N. The plasticity, stress whitening, haze value, durometer and modulus values decreased while the elongation values tended to increase as the level of surface treating agent was increased with an optimum level being about 35–40 weight percent. As the amount of filler treating level was increased, the ease of milling and handling (indicated by the plasticity and recovery values) was also increased. At a 45% treating agent level, the elastomer compositions began to get sticky. Plasticity values of from 160 to 200 mils are considered to be desirable.

TABLE VIII

| Treat Level[1] | Age Of Filler (hours) | Tensile Strength (MPa/psi) | Elong. At Break (%) | Modulus, 100% Elong. (MPa/psi) | Durometer (Shore A) |
|---|---|---|---|---|---|
| 25% | 4 | 11.9/1720 | 400 | 3.0/440 | 78 |
| 25% | 24 | 12.2/1770 | 450 | 201/300 | 67 |
| 30% | 4 | 10.1/1468 | 430 | 1.9/280 | 70 |
| 30% | 24 | 11.8/1710 | 500 | 1.5/220 | 60 |
| 35% | 4 | 12.5/1810 | 560 | 1.8/230 | 65 |
| 35% | 24 | 12.3/1790 | 560 | 1.8/260 | 62 |
| 40% | 4 | 12.3/1790 | 540 | 1.7/240 | 60 |
| 40% | 24 | 11.2/1620 | 625 | 1.1/160 | 53 |
| 45% | 4 | 9.7/1410 | 590 | 1.0/150 | 52 |
| 45% | 24 | 10.8/1560 | 580 | 1.1/160 | 48 |

| Tear, Die B (kN/m/ (ppi)) | Haze Value | Stress Whiten[2] | Plasticity/Recovery (mils) | | | |
|---|---|---|---|---|---|---|
| | | | 1 hour | 1 day | 1 week | 1 month |
| 25.9/148 | 14.3 | 130% E | 356/34 | 343/37 | 391/57 | 378/56 |
| 24.9/142 | 4.6 | 430% E | 310/32 | 307/33 | 351/42 | 350/46 |
| 21.9/125 | 5.5 | 160% E | 300/20 | 302/18 | 351/22 | 280/30 |

TABLE VIII-continued

| | | | | | | |
|---|---|---|---|---|---|---|
| 21.0/120 | 4.2 | 300% E | 278/26 | 278/18 | 250/20 | 254/25 |
| 31.5/180 | 2.8 | 440% E | 240/15 | 269/31 | 276/25 | 255/33 |
| 23.4/134 | 4.6 | none | 227/12 | 234/23 | 242/18 | 228/20 |
| 19.8/133 | 4.5 | none | 188/12 | 193/16 | 199/12 | 204/14 |
| 24.5/140 | 1.7 | 600% E | 138/11 | 129/10 | 147/6 | 154/9 |
| 19.1/109 | 3.0 | 370% E | 102/2 | 127/9 | 138/5 | 140/3 |
| 15.1/86 | 3.3 | 420% E | 121/7 | 99/8 | 111/2 | 114/6 |

[1] Filler surface treatment level is weight percent of total filler
[2] Stress whitening is the elongation (E) value at which an optically clear elastomer tensile bar visually becomes whitened and opaque

TABLE IX

| Treat Level[1] | Age Of Filler (hours) | Tensile Strength (MPa/psi) | Elong. At Break (%) | Modulus 100% Elong. (MPa/psi) | Durometer (Shore A) |
|---|---|---|---|---|---|
| 25% | 4 | TOO HARD TO COMPOUND | | | |
| 25% | 24 | 10.7/1550 | 375 | 3.8/550 | 81 |
| 30% | 4 | 11.4/1660 | 350 | 3.4/500 | 80 |
| 30% | 24 | 12.4/1800 | 500 | 1.9/280 | 70 |
| 35% | 4 | 9.7/1400 | 490 | 2.2/320 | 74 |
| 35% | 24 | 12.0/1740 | 530 | 1.7/240 | 65 |
| 40% | 4 | 10.2/1480 | 550 | 1.5/220 | 63 |
| 40% | 24 | 11.4/1650 | 580 | 1.4/200 | 61 |
| 45% | 4 | 10.5/1520 | 620 | 1.6/230 | 53 |
| 45% | 24 | 10.7/1550 | 600 | 1.0/140 | 50 |

| Tear, Die B (kN/m/ (ppi)) | Haze Value | Stress Whiten[2] | Plasticity/Recovery (mils) | | | |
|---|---|---|---|---|---|---|
| | | | 1 hour | 1 day | 1 week | 1 month |
| TOO HARD TO COMPOUND | | | | | | |
| 16/92 | 7.9 | 350% E | 373/41 | 434/66 | 400/52 | 537/95 |
| 16/94 | 10.4 | 60% E | 360/37 | 369/46 | 402/50 | 468/49 |
| 22.7/130 | 2.8 | 480% E | 277/22 | 277/31 | 305/31 | 350/54 |
| 20.1/115 | 15.4 | 55% E | 286/19 | 282/29 | 312/32 | 320/25 |
| 20.1/115 | 1.8 | 420% E | 229/16 | 229/16 | 275/28 | 254/26 |
| 19.3/110 | 5.3 | 130% E | 212/12 | 194/14 | 216/8 | 231/10 |
| 17/95 | 2.7 | 410% E | 181/8 | 186/15 | 200/12 | 219/17 |
| 21.9/125 | 5.5 | 140% E | 149/10 | 133/10 | 150/5 | 177/12 |
| 18.9/108 | 2.4 | 350% E | 106/3 | 97/6 | 110/3 | 124/7 |

[1] Filler surface treatment level is weight percent of total filler
[2] Stress whitening is the elongation (E) value at which an optically clear elastomer tensile bar visually becomes whitened and opaque

EXAMPLE 7

Silicone elastomers containing the surface-treated silica fillers used in the previous Examples were highly transparent and those having haze values of less than 2.4% at 1.52 mm thickness are considered to be optically clear. A phenomenon referred to as stress whitening was observed (see Example 6) when the sample was elongated and this can be of concern if the elastomer is used in an application which requires that it have a high degree of clarity. One means for greatly reducing or alleviating this phenomenon was to reduce the level of ammonia used to prepare the fillers when the method described in U.S. Pat. No. 4,344,800 was used to prepare the fillers. The previous Examples employed an ammonia ($NH_3$) level of about 0.13 g $NH_3$ per gram of MOS. It was found that the amount of stress whitening could be reduced by decreasing the level of ammonia to from 0.093 to 0.0093 g $NH_3$ per gram of MOS in the filler formulation.

The basic filler formulation employed was 220 ml methanol, 150 ml of MOS and 59.1 g of an equilibrated Reaction Mixture having a molar ratio of $Me_2SiO_{2/2}$:$MeSiO_{3/2}$ of 1:1. The following amounts of Conc. Ammonium Hydroxide and, optionally, water, were used in the above filler formulation to obtain the indicated ammonia concentration level:

| g$NH_3$/g MOS | Conc. Amm. Hydroxide | Water |
|---|---|---|
| 0.093 | 56.4 ml | 0 |
| 0.047 | 28.2 ml | 17.7 ml |
| 0.031 | 18.8 ml | 23.8 ml |
| 0.023 | 14.1 ml | 26.9 ml |
| 0.093 | 5.6 ml | 32.3 ml |

In the above formulations, the Conc. Ammonium Hydroxide was added last in preparing the wet, gelled filler composition. Each filler composition was aged for 24 hours at room temperature. Each filler composition was then compounded with Gum A at a filler loading level of 60 phr in the same manner described for the elastomeric compositions employed in Example 6 and cured as in Example 6. The physical properties of the cured elastomers and plasticity/recovery of the uncured compositions are reported in Table X.

For this series, the cured elastomers did not exhibit stress whitening at or below an ammonia concentration of 0.047 g $NH_3$/g MOS. Reducing the ammonia concentration also resulted in an increase in tensile strength, modulus, durometer, die B tear values and plasticity.

Samples of the fillers prepared using 0.093 g $NH_3$/g MOS and 0.031 g $NH_3$/g MOS were aged 6 weeks at room temperature before they were compounded into elastomers as above. Neither of the cured elastomers prepared from these fillers exhibited stress whitening.

TABLE X

| $NH_3$ Level (g $NH_3$/g MOS) | Tensile Strength (MPa/psi) | Elongation (%) | Modulus, 100% Elong. (MPa/psi) | Durometer (Shore A) |
|---|---|---|---|---|
| 0.13 | 11.2/1620 | 625 | 1.1/160 | 53 |
| 0.093 | 11.4/1650 | 600 | 1.2/180 | 58 |
| 0.047 | 11.7/1700 | 640 | 1.5/220 | 59 |
| 0.031 | 13.1/1900 | 610 | 1.9/280 | 64 |
| 0.023 | 12.7/1840 | 580 | 2.1/300 | 65 |
| 0.0093 | 10.3/1500 | 570 | 2.3/330 | 65 |

| Tear, Die B (kN/m/ (ppi)) | Haze Value | Stress Whiten[1] | Plasticity/Recovery | | | |
|---|---|---|---|---|---|---|
| | | | 1 hour | 1 day | 1 week | 1 month |
| 24.5/140 | 1.7 | 600% E | 138/11 | 139/10 | 147/16 | 154/9 |
| 23.4/134 | 1.5 | 550% E | 161/7 | 155/5 | 175/9 | 170/9 |
| 28.7/164 | 2.9 | none | 205/13 | 215/13 | 217/10 | 235/20 |
| 26.8/153 | 3.0 | none | 248/26 | 262/29 | 257/28 | 271/33 |
| 27.0/154 | 2.0 | none | 266/26 | 271/29 | 273/31 | 288/36 |
| 28.4/162 | 1.5 | none | 269/26 | 275/30 | 284/32 | 301/41 |

[1] Stress whitening is the elongation (E) value at which an optically clear elastomer tensile bar visually becomes whitened and opaque

EXAMPLE 8

This Example demonstrates the use of the equilibrated reaction mixtures of the present invention to surface-treat a preformed, reinforcing silica filler. That filler (hereinafter "Fume Silica") was reportedly prepared by the flame hydrolysis of tetrachlorosilane and was commercially obtained from Cabot Corporation, Boston, MA under the trademark CAB-O-SIL ®MS-75. The manufacturer reports that the surface area (BET Method) of that filler was 255±15 square meters per gram.

For comparative purposes, a sample of Fume Silica was surface-treated with hexamethyldisilazane (100 parts by weight of filler/30 parts by weight of hexamethyldisilazane) in the presence of a small amount of water and that filler was believed to contain about 21 weight percent of surface treating agent in the form of Me₃SiO₁/₂ units (Run No. 20).

Each of the following amounts of an equilibrated reaction mixture having a molar ratio of $Me_2SiO_{2/2}$:$MeSiO_{3/2}$ of 1:1 were tumbled with 40 g of Fume Silica in a sealed metal can for about 2.5 days at room temperature to obtain a surface-treated silica filler: 8.6 g (Run No. 21), 15.4 g (Run No. 22), and 40 g (Run No. 23), respectively. Likewise, 11.9 g (Run No. 24) and 31.74 g (Run No. 25), respectively, of an equilibrated reaction mixture having a molar ratio of $Me_2SiO_{2/2}$:$MeSiO_{3/2}$ of 4:1 were each tumbled overnight at room temperature in a sealed metal can with 40 g of Fume Silica to obtain a surface-treated silica filler.

To check the effect of a basic catalyst on surface-treatment, the following mixture was tumbled together overnight at room temperature in a sealed metal can to obtain a surface-treated silica filler: 40 g Fume Silica, 31.74 g of the above 1:4 molar ratio Reaction Mixture and 2.6 g ammonium carbonate (Run No. 26). To determine the filler surface-treatment level of the fillers, the fillers were placed in an oven for 2 hours at 150° C. and the weight loss on heating was calculated. Since the metal cans were sealed, the loss in weight upon heating was attributed to filler surface-treatment loss and the amount of filler surface-treatment levels reported in Table XI were calculated from this weight loss.

Another sample of Fume Silica was surface-treated (Run No. 27) by tumbling a mixture of 15 g Fume Silica, 15 g of an equilibrated reaction mixture having a molar ratio of $Me_2SiO_{2/2}$:$MeSiO_{3/2}$ of 1:1, 55 g methanol and 2 g Conc. Ammonium Hydroxide.

Each of the above fillers was compounded into elastomeric compositions with Gum A at a filler loading level (filler nonvolatile solids) of 50 phr. The elastomer composition was catalyzed with 0.7 phr of Peroxide A and cured as in Example 2. The physical properties of the cured elastomers are reported in Table XI beside the headings Run Nos. 20 to 27.

Finally, the use of an equilibrated reaction mixture having a molar ratio of $Me_2SiO_{2/2}$:$MeSiO_{3/2}$ of 1:1 was employed as a plasticizer for a mixture of Fume Silica and Gum A. Two elastomeric compositions were prepared. Run No. 28 had the following formulation: 25 g Gum A, 10 g Fume Silica, 3.75 g (2.5 g nonvolatile treating agent) of the 1:1 molar ratio reaction mixture and 0.175 g Peroxide A. Run No. 29 had the following formulation: 25 g Gum A, 7.5 g Fume Silica, 7.5 g (5 g nonvolatile treating agent) and 0.175 g Peroxide A. Each formulation was calculated to have 12.5 g filler nonvolatile solids with the filler used in Run 29 having a filler surface treatment level (40 weight percent) twice that of the filler of Run 28 (20 weight percent). The Gum A was placed on a two-roll mill, one-fourth of the Fume Silica was blended into the gum followed by one-fourth of the reaction mixture. This process was repeated three more times. After all the silica and reaction mixture was added, the mixture was milled 10 minutes at 110° C., cooled to room temperature and the Peroxide A was milled into the mixture. Each formulation was, then cured as in Example 2 and the physical properties obtained are reported in Table XI.

Run Nos. 21-23 gave lower haze values than the other Run Nos. 20 and 24-29, had better uncured plasticity values than Run No. 20, and had the highest tear values of this series of Runs. The properties obtained with Run 29 were comparable to that obtained for comparative Run No. 20.

TABLE XI

| Run No. | Surface Treatment Level (wt. %) | Tensile Strength (MPa/psi) | Elongation (%) | Modulus, 100% Elongation (MPa/psi) |
|---|---|---|---|---|
| 20 | 21 | 9.24/1340 | 550 | 0.8/120 |
| 21 | 9.5 | 10.3/1500 | 460 | 1.2/180 |
| 22 | 12.4 | 11.2/1630 | 490 | 1.4/210 |
| 23 | 18.7 | 8.3/1200 | 700 | 0.7/100 |
| 24 | 12.6 | 9.1/1320 | 470 | 1.2/175 |
| 25 | 30.3 | 9.2/1330 | 640 | 0.8/120 |
| 26 | 24 | 9.6/1390 | 840 | 0.6/80 |
| 27 | — | 9.5/1375 | 750 | 0.6/80 |
| 28 | — | 9.5/1375 | 415 | 1.1/160 |
| 29 | — | 7.6/1100 | 530 | 0.8/120 |

| Run No. | Durometer (Shore A) | Tear, Die B (kN/m/ppi) | Haze Value (%) | Plasticity/Recovery (mils) |
|---|---|---|---|---|
| 20 | 41 | 10.9/62 | 21.8 | 73/6 |
| 21 | 58 | 14.4/82 | 12.5 | 126/2 |
| 22 | 54 | 20.3/116 | 11.6 | 109/4 |
| 23 | 46 | 26.8/153 | 13.6 | 91/4 |
| 24 | 58 | 11.9/68 | 24.5 | 90/5 |
| 25 | 45 | 12.6/72 | 22.6 | 72/4 |
| 26 | 36 | 17.5/100 | 33.1 | 65/5 |
| 27 | 37 | 9.6/55 | 19.4 | — |
| 28 | 57 | 10.0/57 | 18.5 | — |
| 29 | 46 | 10.2/58 | 20.9 | — |

That which is claimed is:

1. A method of surface treating a particulate inorganic filler which comprises the steps of
   (A) contacting 100 parts by weight of a particulate inorganic filler with a surface treating agent comprising at least one component which is an equilibrated reaction mixture consisting essentially of $R_2SiO_{2/2}$ units, $RSiO_{3/2}$ units and $CH_3O_{1/2}$ radicals, there being A moles of $R_2SiO_{2/2}$ units per mole of $RSiO_{3/2}$ units present in said mixture and B moles of said $CH_3O_{1/2}$ radicals, said A having an average value of from 0.5 to 10 and B having an average value of from 3 to 6, the value of B being related to A such that when A=0.5, B=6 and when A=10, B=3, and wherein R is selected from the group consisting of hydrocarbon radicals of from 1 to 10 inclusive carbon atoms and haloalkyl radicals of from 1 to 10 inclusive carbon atoms, said reaction mixture (1) having been prepared by equilibration in the presence of a catalyst for the equilibration reaction and (2) having an overall average molecular weight of less than 500, there being at least 5 and up to 50 parts of weight of said equilibrated reaction mixture based on the total weight of $R_2SiO_{2/2}$ and $RSiO_{3/2}$ units present in the mixture per 100 parts by weight of said filler, and
   (B) maintaining said surface-treating agent in contact with said filler for a sufficient amount of time to obtain a hydrophobic, surface-treated particulate inorganic filler.

2. The method as claimed in claim 1 wherein said reaction mixture is obtained by equilibrating a mixture of (1) cyclic polydiorganosiloxanes of the average formula $(R_2SIO)_x$ and (2) $RSi(OCH_3)_3$ wherein the amounts of (1) and (2) are selected such that the equilibrated reaction mixture has a molar ratio of $R_2SiO_{2/2}$:$RSiO_{3/2}$ units in the range of 0.5:1 to 10:1, said x having an average value of from 3 to 7.

3. The method as claimed in claim 2 wherein the inorganic filler is a silica filler having a surface area of at least 50 m²/g, the ratio of $R_2SiO_{2/2}$:$RSiO_{3/2}$ is in the range of 0.75:1 to 4:1 and at least 70 weight percent of the cyclic polysiloxanes are cyclic polysiloxanes wherein $x=4$, and wherein more than 50 mole percent of the total moles of R radicals present in said reaction mixture are methyl radicals.

4. The method as claimed in claim 3 wherein R is selected from the group consisting of methyl and vinyl radicals, no more than 10 mole percent of the total moles of R radicals present in said reaction mixture being vinyl radicals.

5. The method as claimed in claim 3 wherein the ratio of $R_2SiO_{2/2}$:$RSiO_{3/2}$ is in the range of 0.9:1 to 1.1:1.

6. The method as claimed in claim 5 wherein R is selected from the group consisting of methyl and vinyl radicals, no more than 10 mole percent of the total moles of R radicals present in said reaction mixture being vinyl radicals.

7. A hydrophobic, surface-treated particulate inorganic filler which has been surface treated in accordance with the method of claim 1.

8. A hydrophobic, surface-treated particulate inorganic filler which has been surface treated in accordance with the method of claim 2.

9. A hydrophobic, surface-treated particulate silica filler which has been surface treated in accordance with the method of claim 3.

10. A hydrophobic, surface-treated particulate silica filler which has been surface treated in accordance with the method of claim 4.

11. A hydrophobic, surface-treated particulate silica filler which has been surface treated in accordance with method of claim 5.

12. A hydrophobic, surface treated particulate silica filler which has been surface treated in accordance with the method of claim 6.

13. A composition curable to a silicone elastomer comprising from 50 to 97.5 parts by weight of at least one polydiorganosiloxane and from 2.5 to 50 parts by weight of a particulate inorganic filler which has been surface treated in accordance with the method of claim 1.

14. The curable composition as claimed in claim 13 wherein said reaction mixture is obtained by equilibrating a mixture of (1) cyclic polydiorganosiloxanes of the average formula $(R_2SiO)_x$ and (2) $RSi(OCH_3)_3$ wherein the amount of (1) and (2) are selected such that the equilibrated reaction mixture has a molar ratio of $R_2SiO_{2/2}$:$RSiO_{3/2}$ units in the range of 0.5:1 to 10:1.

15. The curable composition as claimed in claim 14 wherein the inorganic filler is a silica filler having a surface area of at least 50 m$^2$/g, the ratio of $R_2SiO_{2/2}$:$RSiO_{3/2}$ is in the range of 0.75:1 to 4:1 and at least 70 weight percent of the cyclic polysiloxanes are cyclic polysiloxanes wherein $x=4$.

16. The curable composition as claimed in claim 15 wherein R is selected from the group consisting of methyl and vinyl radicals, no more then 10 mole percent of the total moles of R radicals present in said reaction mixture being vinyl radicals.

17. The curable composition as claimed in claim 16 wherein the ratio of $R_2SiO_{2/2}$:$RSiO_{3/2}$ is in the range of 0.9:1 to 1.1:1.

18. The curable composition as claimed in claim 17 wherein R is selected from the group consisting of methyl and vinyl radicals, no more than 10 mole percent of the total moles of R radicals present in said reaction mixture being vinyl radicals.

19. A cured elastomer comprising the product obtained upon curing the composition of claim 13.

20. A cured elastomer comprising the product obtained upon curing the composition of claim 14.

21. A cured elastomer comprising the product obtained upon curing the composition of claim 15.

22. A cured elastomer comprising the product obtained upon curing the composition of claim 17.

23. A cured elastomer comprising the product obtained upon curing the composition of claim 18.

24. The cured elastomer of claim 20 which is in the form of a prosthetic device.

25. The cured elastomer of claim 21 which is in the form of a prosthetic device.

26. The cured elastomer of claim 22 which is in the form of a prosthetic device.

27. The cured elastomer of claim 23 which is in the form of a prosthetic device.

* * * * *